United States Patent [19]

Algieri et al.

[11] 4,200,578
[45] Apr. 29, 1980

[54] THIAZOLE DERIVATIVES

[75] Inventors: Aldo A. Algieri, Fayetteville; Ronnie R. Crenshaw, Dewitt, both of N.Y.

[73] Assignee: Bristol-Myers Company, New York, N.Y.

[21] Appl. No.: 970,517

[22] Filed: Dec. 18, 1978

[51] Int. Cl.² .................................... C07D 277/20
[52] U.S. Cl. .................................... 548/193; 424/270; 548/197; 548/205
[58] Field of Search .................... 260/306.8 R, 30 RR

[56] References Cited

U.S. PATENT DOCUMENTS

| 4,022,797 | 5/1977 | Durant et al. | 260/302 R |
| 4,072,748 | 2/1978 | Durant et al. | 424/270 |
| 4,112,234 | 9/1978 | Crenshaw et al. | 548/342 |

FOREIGN PATENT DOCUMENTS

| 804144 | 9/1972 | Belgium . |
| 841814 | 5/1976 | Belgium . |
| 78/2129 | 4/1978 | South Africa . |
| 1421792 | 5/1974 | United Kingdom . |

OTHER PUBLICATIONS

Gannellin et al., Federation Proceedings, 35 (1924 (1976), Drugs of the Future, 1, 13(1976).

Primary Examiner—Nicholas S. Rizzo
Attorney, Agent, or Firm—Richard R. Lloyd

[57] ABSTRACT

Compounds of the formula

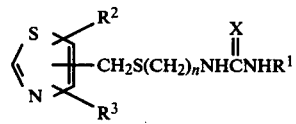

wherein $R^1$ is a straight or branched chain alkynyl group containing from 3 to 9 carbon atoms, inclusive; $R^2$ and $R^3$ each are independently hydrogen, (lower)alkyl, guanidino or $-(CH_2)_pNR^4R^5$; $R^4$ and $R^5$ each are independently hydrogen, (lower)alkyl or phenyl; n is 2 or 3; p is 1, 2 or 3; X is $NR^6$ or $CHR^6$; $R^6$ is cyano, nitro, $SO_2Ar$ or $SO_2$(lower)alkyl; and Ar is phenyl or phenyl containing 1 or 2 substituents selected from halogen and (lower)alkyl; and nontoxic, pharmaceutically acceptable salts thereof, are potent anti-ulcer agents.

16 Claims, No Drawings

THIAZOLE DERIVATIVES

SUMMARY OF THE INVENTION

This application relates to certain N-alkynyl-N'-{ω-[(optionally substituted thiazolyl)methylthio]alkyl}-derivatives of N''-cyanoguanidine and of 1,1-diamino-2-substituted ethylene, which are histamine $H_2$-receptor blocking agents, which inhibit gastric secretion and which are useful in the treatment of ulcers, and to processes for their preparation.

BACKGROUND AND PRIOR ART

The clinical objective in treatment of peptic ulcer disease is to decrease gastric acid secretion, based on the principle "no acid, no ulcer." Traditional peptic ulcer disease therapy involves control of diet and the use of antacids and anticholinergics.

There is evidence indicating that histamine may be the final common pathway for stimulation of gastric secretion. This effect of histamine is mediated via $H_2$-reeceptors and is not inhibited by the classical antihistamines, which are $H_1$-receptor blockers. A number of specific $H_2$-receptor blocking agents ($H_2$-receptor antagonists) are now known. These compounds inhibit basal acid secretion, as well as secretion by other known gastric acid stimulants, and are useful in the treatment of peptic ulcers.

Burimamide (IIa) was the first clinically effective $H_2$-receptor antagonist. It inhibits gastric secretion in animals and man, but oral absorption is poor.

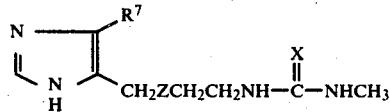

II

| | | | |
|---|---|---|---|
| IIa; | $R^7 = H$, $Z = CH_2$, $X = S$ | | Burimamide |
| b; | $R^7 = CH_3$, $Z = S$, $X = S$ | | Metiamide |
| c; | $R^7 = CH_3$, $Z = S$, $X = NCN$ | | Cimetidine |

Metiamide (IIb), a subsequently evaluated $H_2$ antagonist, is more potent than burimamide and is orally active in man. Clinical utility was limited, however, owing to toxicity (agranulocytosis). Cimetidine (IIc) is as effective an $H_2$ antagonist as metiamide, without producing agranulocytosis, and has recently been marketed as an anti-ulcer drug. The half-life of cimetidine is relatively short, thereby necessitating a therapeutic regimen of multi daily doses of 200-300 mg. tablets. There is thus a need for anti-ulcer agents which are longer acting and/or more potent than cimetidine.

Reviews on the development of $H_2$ antagonists, including those discussed in the preceding paragraph, may be found in C. R. Ganellin, et. al., *Federation Proceedings*, 35, 1924 (1976), in *Drugs of the Future*, 1, 13 (1976), and in references cited therein. Relevant patents are as follows:

Belgian Pat. No. 841,814 (Farmdoc 90568X) discloses inhibitors of histamine-stimulated gastric secretion having the formula

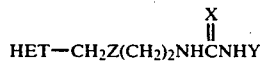

in which HET is one of eight named heterocyclic rings (including thiazole) which may be substituted by (lower)alkyl, hydroxyl, amino or halogen; Z is sulfur or $CH_2$; X is S, $CHNO_2$, NCN or NH; Y is $NH_2$, (lower)alkylamino, di(lower)alkylamino, (lower)alkoxy, phenylethyl, imidazolylethyl, allyl, trifloroethyl or $(CH_2)_nR$; n is 1-12; and R is OH, (lower)alkoxy, $NH_2$ or (lower)alkylamino; provided that, when X is NH, Y is trifloroethyl or $(CH_2)_nR$; and when X is NCN, Y may not be amino or (lower)alkylamino.

Belgian Pat. No. 804,144 (Farmdoc 19437V) discloses inhibitors of histamine-stimulated gastric acid secretion having the formula

in which HET is a 5 or 6 membered heterocyclic ring containing nitrogen (thiazole is named), which may be substituted by alkyl, halogen, $CF_3$, OH or $NH_2$; m and n are each 0–4 and the sum of m and n is from 2 to 4; Z is sulfur, oxygen, NH or $CH_2$; and $R_1$ is hydrogen or (lower)alkyl.

U.K. Pat. No. 1,421,792 discloses $H_2$-receptor inhibitors of the formula

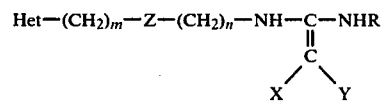

wherein X and Y, which may be the same or different, are hydrogen, nitro, cyano or $SO_2Ar$, but may not both be hydrogen; R is hydrogen, (lower)alkyl or $Het(CH_2)_mZ(CH_2)_n$; Z is sulfur or methylene; m is 0, 1 or 2 and n is 2 or 3 provided that the sum of m and n is 3 or 4; Het is an imidazole, pyridine, thiazole, isothiazole, oxazole, isoxazole, triazole or thiadiazole ring which is optionally substituted by (lower)alkyl, hydroxy, halogen or amino; and Ar is phenyl, optionally substituted by halogen, methyl or amino.

U.S. Pat. No. 4,072,748 discloses histamine $H_2$-receptor inhibitors of the formula

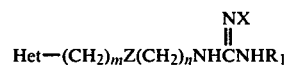

wherein Het is a nitrogen containing 5 or 6 membered heterocyclic ring (thiazole is one of 12 named heterocyclic rings) optionally substituted by (lower)alkyl, trifluoromethyl, hydroxyl, halogen or amino; Z is sulfur, oxygen, NH or a methylene group; m is 0, 1 or 2 and n is 2 or 3, the sum of m and n being from 2 to 4; X is $COR_3$; $CSR_3$, $SO_2R_4$, $NCHR_5$ or, when Z is methylene, may be nitro; $R_3$ is (lower)alkyl, (lower)alkoxy or amino; $R_4$ is (lower)alkyl, trifluoromethyl, amino or substituted or unsubstituted aryl, such as phenyl optionally substituted by halogen, (lower)alkyl or amino; $R_5$ is substituted or unsubstituted aryl, such as phenyl; and $R_1$ is hydrogen or (lower)alkyl such as methyl; and pharmaceutically acceptable salts thereof.

U.S. Pat. No. 4,022,797 discloses histamine $H_2$-receptor inhibitors of the formula

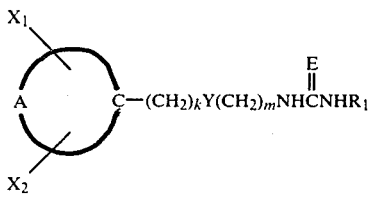

wherein A, taken together with the carbon atom, forms an imidazole, pyrazole, pyrimidine, pyrazine, pyridazine, thiazole, isothiazole, oxazole, isoxazole, triazole, thiadiazole, benzimidazole or 5,6,7,8-tetrahydro[1,5-a]-pyridine ring; $X_1$ is hydrogen, (lower)alkyl, hydroxyl, trifluoromethyl, benzyl, halogen, amino or

$X_2$ is hydrogen or, when $X_1$ is (lower)alkyl, may be (lower)alkyl or halogen; k is 0 to 2 and m is 2 to 3, provided that the sum of k and m is 3 or 4; Y is oxygen, sulfur or NH; E is $NR_2$; $R_1$ is hydrogen, (lower)alkyl or di(lower)alkylamino(lower)alkyl; and $R_2$ is hydrogen, nitro or cyano; and pharmaceutically acceptable addition salts thereof.

South African Pat. No. 78/2129 discloses histamine $H_2$-receptor antagonists of the formula

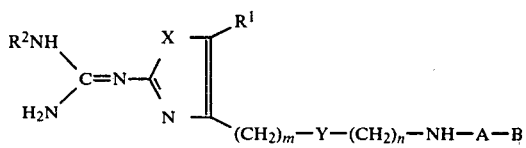

in which X is sulfur or NH; Y is oxygen, sulfur, a direct bond, methylene, sulfinyl or a cis or trans vinylene radical; m is 0 to 4 and n is 1 to 4, provided that, when Y is sulfur, oxygen or sulfinyl, m is 1 to 4, and when Y is oxygen or sulfinyl, n is 2 to 4; $R^1$ is hydrogen, halogen or (lower)alkyl; $R^2$ is hydrogen, (lower)alkyl, (lower)alkanoyl or an aroyl group of from 7 to 11 carbon atoms; A is 3,4-dioxocyclobuten-1,2-diyl or a group of the formula C=Z in which Z is oxygen, sulfur, NCN, $NNO_2$, $CHNO_2$, $NCONH_2$, $C(CN)_2$, $NCOR^3$, $NCO_2R^3$, $NSO_2R^3$ or $NR^4$ in which $R^3$ is (lower)alkyl or an aryl group of from 6 to 12 carbon atoms, and $R^4$ is hydrogen or (lower)alkyl; B is (lower)alkoxy, (lower)alkylthio or $NR^5R^6$ in which $R^5$ and $R^6$ each are independently hydrogen, alkyl of from 1 to 10 carbon atoms, alkenyl of from 3 to 10 carbon atoms in which the double bond is seperated from the nitrogen atom by at least one carbon atom, cycloalkyl of from 3 to 8 carbon atoms, (primary hydroxy)alkyl of from 2 to 6 carbon atoms in which the oxygen atom is seperated from the nitrogen atom by at least two carbon atoms, alkoxyalkyl radicals of from 3 to 10 carbon atoms in which the oxygen atom is seperated from the nitrogen atom by at least two carbon atoms, alkylaminoalkyl of from 3 to 10 carbon atoms in which the nitrogen atom is separated from the nitrogen atom of $NR^5R^6$ by at least two carbon atoms, or dialkylaminoalkyl of from 4 to 10 carbon atoms in which the nitrogen atom is separated from the nitrogen atom of $NR^5R^6$ by at least two carbon atoms; and the pharmaceutically acceptable acid-addition salts thereof.

U.S. Pat. No. 4,112,234 discloses histamine $H_2$-receptor inhibitors of the formula

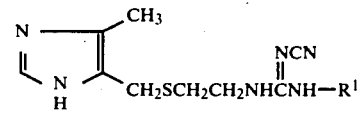

wherein $R^1$ is a straight or branched chain alkynyl group containing from 3 to 9 carbon atoms, and processes for the preparation thereof.

This application relates to histamine $H_2$-receptor antagonists which are effective inhibitors of gastric secretion in animals, including man, which are useful in the treatment of peptic ulcer disease and which have the formula

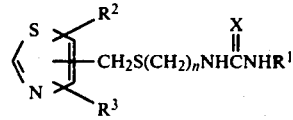

wherein $R^1$ is a straight or branched chain alkynyl group containing from 3 to 9 carbon atoms, inclusive; $R^2$ and $R^3$ each are independently hydrogen, (lower)alkyl, guanidino or $-(CH_2)_pNR^4R^5$; and $R^4$ and $R^5$ each are independently hydrogen, (lower)alkyl or phenyl; n is 2 or 3; p is 1, 2 or 3; X is $NR^6$ or $CHR^6$; $R^6$ is cyano, nitro, $SO_2Ar$ or $SO_2$(lower)alkyl; and Ar is phenyl or phenyl containing 1 or 2 substituents selected from halogen and (lower)alkyl; and nontoxic, pharmaceutically acceptable salts thereof.

A preferred embodiment of the invention is a compound of the formula

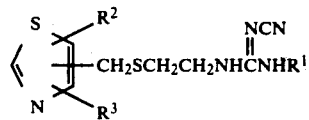

wherein $R^1$, $R^2$ and $R^3$ are as defined above, or a nontoxic, pharmaceutically acceptable salt thereof.

Another preferred embodiment of the invention is a compound of the formula

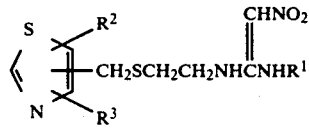

wherein $R^1$, $R^2$ and $R^3$ are as defined above, or a nontoxic, pharmaceutically acceptable salt thereof.

Another preferred embodiment of the invention is a compound of the formula

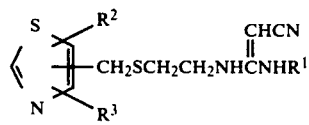

wherein R¹, R² and R³ are as defined above, or a nontoxic pharmaceutically acceptable salt thereof.

Another preferred embodiment of the invention is a compound of the formula

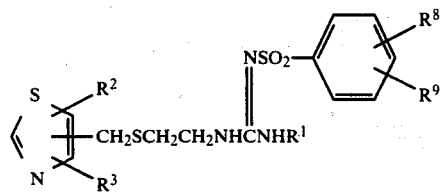

wherein R¹, R² and R³ are as defined above, and R⁸ and R⁹ each are independently hydrogen, halogen or (lower)alkyl, or a nontoxic, pharmaceutically acceptable salt thereof.

Another preferred embodiment of the invention is a compound of the formula

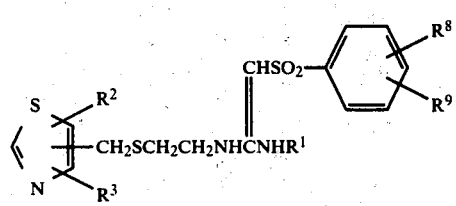

wherein R¹, R² and R³ are as defined above, and R⁸ and R⁹ each are independently hydrogen, halogen or (lower)alkyl, or a nontoxic, pharmaceutically acceptable salt thereof.

A more preferred embodiment of the invention is a compound of the formula

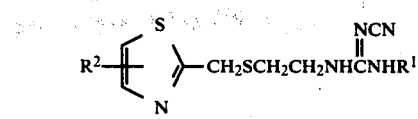

wherein R¹ and R² are as defined above, or a nontoxic pharmaceutically salt thereof.

Another more preferred embodiment of the invention is a compound of the formula

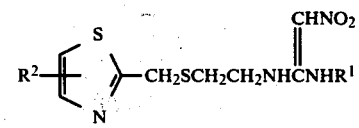

wherein R¹ and R² are as defined above, or a nontoxic, pharmaceutically acceptable salt thereof.

Another more preferred embodiment of the invention is a compound of the formula

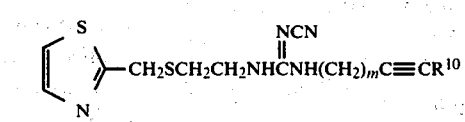

wherein m is an integer of from 1 to 6, inclusive; and R¹⁰ is hydrogen or methyl; or a nontoxic, pharmaceutically acceptable salt thereof.

Another more preferred embodiment of the invention is a compound of the formula

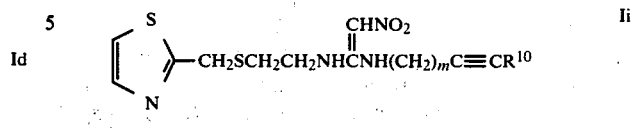

wherein m is an integer of from 1 to 6, inclusive; and R¹⁰ is hydrogen or methyl; or a nontoxic, pharmaceutically acceptable salt thereof.

Another more preferred embodiment of the invention is a compound of the formula

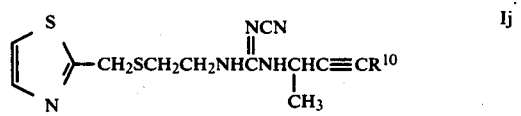

wherein R¹⁰ is hydrogen or methyl; or a nontoxic, pharmaceutically acceptable salt thereof.

Another more preferred embodiment of the invention is a compound of the formula

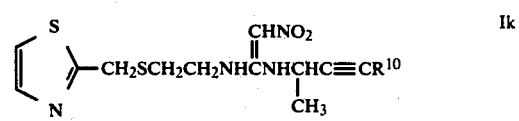

wherein R¹⁰ is hydrogen or methyl, or a nontoxic, pharmaceutically acceptable salt thereof.

A most preferred embodiment of the invention is a compound of the formula

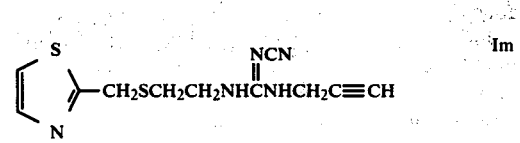

or a nontoxic, pharmaceutically acceptable salt thereof.

Another most preferred embodiment of the invention is a compound of the formula

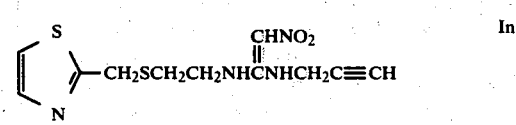

or a nontoxic, pharmaceutically acceptable salt thereof.

Another most preferred embodiment of the invention is a compound of the formula

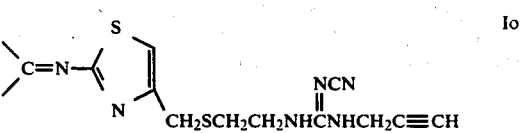

or a nontoxic, pharmaceutically acceptable salt thereof.

Another most preferred embodiment of the invention is a compound of the formula

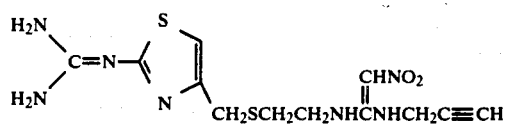

or a nontoxic, pharmaceutically acceptable salt thereof.

Although the compounds of this invention have been shown as having the structure of Formula I, it will be appreciated by those skilled in the art that the compounds in which X is $CHR^6$ can exist is various tautomeric forms, as follows:

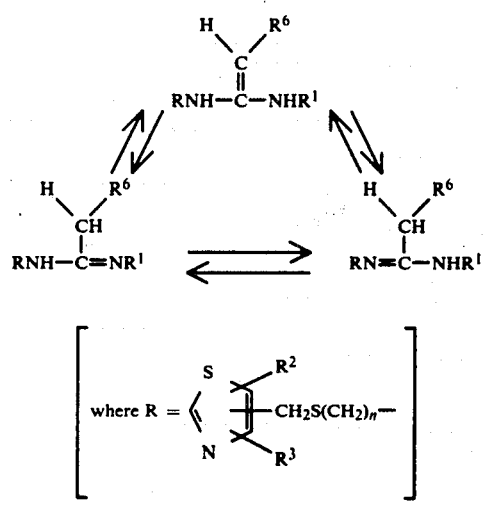

Also, the compounds in which X is $CHR^6$ may exist as two geometric isomers, i.e., cis/trans isomers about the double bond. In addition, all the compounds of Formula I which contain a branched chain alkynyl group as substituent $R^1$ may exist as their d- or l-optical isomers as well as their racemic forms. Thus, for example, 3-amino-1-butyne of the formula

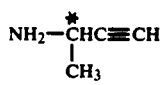

may be resolved into its d- and l- isomers as described by A. Marszak-Fleury, *Compt. rend.*, 242, 1046 (1956). The use of the d- or l- isomer of the alkynylamine in the preparation of a compound of Formula I produces the corresponding d- or l- isomer of the compound of Formula I. The present invention includes within its scope all possible tautomeric forms, geometric isomers and optical isomers of the compounds of Formula I as well as mixtures thereof.

The compounds of the present invention may be prepared by various alternative reaction schemes, as illustrated below for the two most preferred embodiments, compounds Im and In.

Scheme I

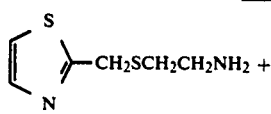

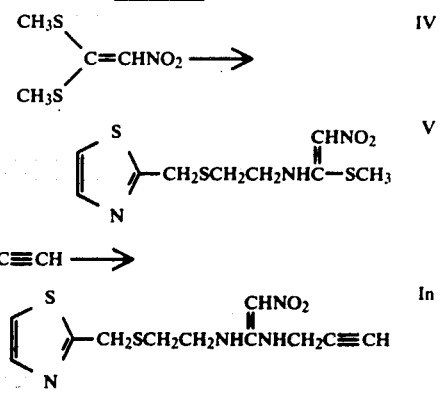

The reaction of compounds III and IV to produce compound V is described in U.S. Pat. No. 4,046,907. Analogous and homologous compounds are prepared by starting with the appropriate analog or homolog of compound III, which may be prepared by known procedures. The compound of formula IV is prepared by procedures described in *Chem. Ber.*, 100, 591 (1967) or *Acta Chem. Scand.*, 21, 2797 (1967). The reaction steps of Scheme I are conducted in a nonreactive solvent such as isopropyl alcohol at or above room temperature. The alkynylamines utilized as starting materials (propargylamine illustrated above) are either commercially available or may be prepared by procedures described in *Bull. Soc. Chim. Fr.*, 490 (1958), *Bull. Soc. Chim. Fr.*, 588 (1967), *Bull. Soc. Chim. Fr.*, 592 (1967), *Annales de Chimie* (Paris), 3, 656 (1958) and *J. Org. Chem.*, 21, 791 (1956).

Scheme II

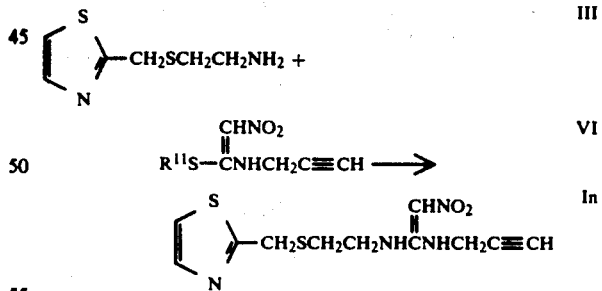

The reaction is conducted in a non-reactive solvent such as methanol at or above room temperature. As will be appreciated by those skilled in the art, $R^{11}$ may be any substituent such that $-SR^{11}$ will be a suitable leaving group. Such leaving groups are conventional in the art. Thus, $R^{11}$ may be (lower)alkyl, aryl or substituted aryl (e.g. p-nitrophenyl), or the like. The compounds of Formula VI may themselves be prepared by alternative procedures, such as illustrated below for the preparation of Compound VI wherein $R^{11}$ is methyl.

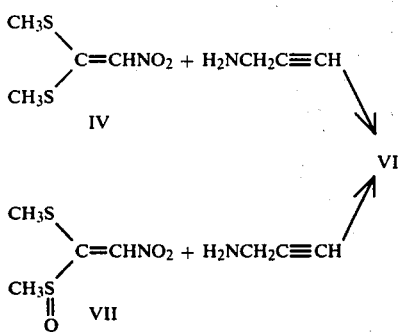

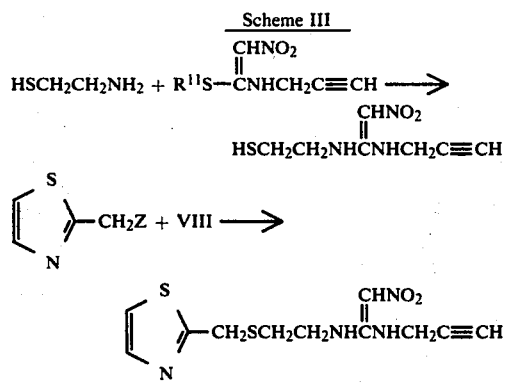

The compound of Formula VII is prepared by the procedures described in Belgian Pat. No. 841,526 and analogous compounds may be prepared by analogous procedures. It will be apparent to those skilled in the art that, if the propargylamine utilized above is replaced by a different alkynylamine, there will be produced a compound of Formula VI which contains the different alkynyl group. That compound, in turn, can be reacted with a compound of Formula III to produce a compound of Formula I containing the different alkynyl group.

Scheme III

HSCH$_2$CH$_2$NH$_2$ + R$^{11}$S—C(=CHNO$_2$)NHCH$_2$C≡CH ⟶    VI

HSCH$_2$CH$_2$NHC(=CHNO$_2$)NHCH$_2$C≡CH    VIII

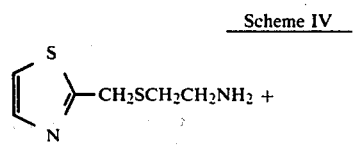

The reaction steps are conducted in a non-reactive solvent at or above room temperature. Compound VI is prepared as described above in Scheme II. Substituent Z in Compound IX is a conventional leaving group. Suitable leaving groups "Z" for use in this reaction are well-known to those skilled in the art. They include, for example, fluoro, chloro, bromo, iodo, —O$_3$SR$^{12}$ wherein R$^{12}$ is (lower)alkyl [e.g. methanesulfonate], —O$_3$SR$^{13}$ wherein R$^{13}$ is aryl or substituted aryl [e.g. benzenesulfonate, p-bromobenzenesulfonate or p-toluenesulfonate], —O$_3$SF, acetoxy and 2,4-dinitrophenoxy. For convenience and economy we normally prefer to utilize compound IX in which Z is chloro. The compound of Formula IX, and analogous compounds, are either commercially available or may be prepared by general procedures described in Zh. Obshch. Khim., 31, 1356 (1961) [C.A., 55, 24719f (1961)] and the references cited in Example 15, below.

Scheme IV

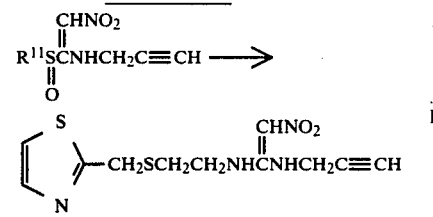

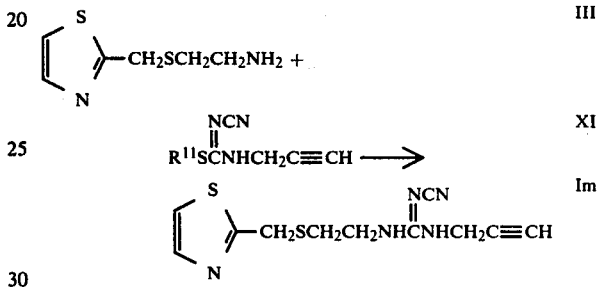

The reaction is conducted in a non-reactive solvent at or above room temperature. The compound of Formula X, in which R$^{11}$ is as described above, is prepared by oxidation of a compound of Formula VI by conventional means.

Scheme V

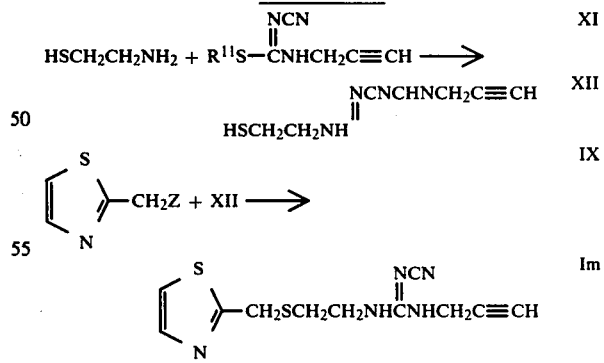

The reaction is conducted in a non-reactive solvent or at above room temperature. The compounds of Formula XI may be prepared by procedures described in our colleagues U.S. patent application Ser. No. 936,668, filed Aug. 24, 1978, the complete disclosure of which is incorporated herein by reference. For example, Compound XI in which R$^{11}$ is methyl may be prepared by reacting dimethyl cyanodithioimidocarbonate with propargylamine. The dimethyl cyanodithioimidocarbonate may itself be prepared by procedures described in J. Org. Chem., 32, 1566 (1967). Analogous compounds may be prepared by analogous procedures.

Scheme VI

HSCH$_2$CH$_2$NH$_2$ + R$^{11}$S—C(=NCN)NHCH$_2$C≡CH ⟶    XI

HSCH$_2$CH$_2$NHC(=NCN)NHCH$_2$C≡CH    XII

The reaction, which is analogous to that described in Scheme III above, is conducted in a non-reactive solvent at or above room temperature. The compound of Formula XII and homologous and analogous compounds containing other alkynyl groups are described and claimed in our colleagues U.S. patent application Ser. No. 906,901, filed May 18, 1978, the complete disclosure of which is incorporated herein by reference.

Scheme VII

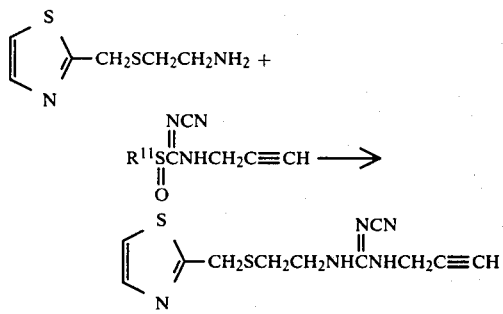

The reaction, which is analogous to that described in Scheme IV above, is conducted in a non-reactive solvent at or above room temperature. The compounds of Formula XIII are prepared by oxidation of a compound of Formula XI by conventional means.

Scheme VIII

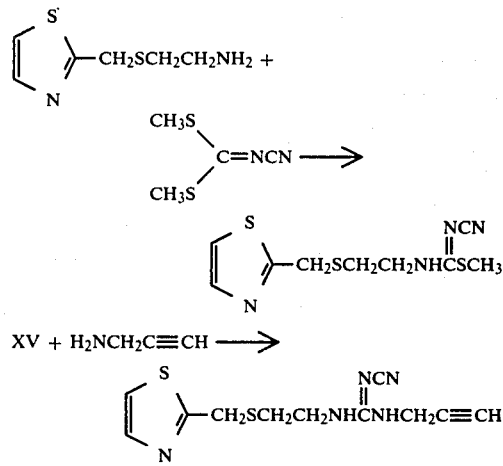

This reaction, which is analogous to that described in Scheme I above, is conducted in an inert solvent at or above room temperature. The compound of Formula XIV is prepared by the procedure described in *J. Org. Chem.*, 32, 1566 (1967). The compound of Formula XV is itself disclosed in U.S. Pat. No. 3,950,333. Analogs and homologs of Compound XV are prepared by starting with the corresponding analogs or homologs of Compound III.

As used herein, the term nontoxic pharmaceutically acceptable salt means the mono- or di-salt of a compound of this invention with a nontoxic pharmaceutically acceptable organic or inorganic acid. Such acids are well known and include hydrochloric, hydrobromic, sulfuric, sulfamic, phosphoric, nitric, maleic, fumaric, succinic, oxalic, benzoic, methanesulfonic, ethanedisulfonic, benzenesulfonic, acetic, propionic, tartaric, citric, camphorsulfonic, and the like. The salts are made by methods known in the art.

The term "(lower)alkyl," as used herein, means a straight or branched chain alkyl group containing from 1 to 6 carbon atoms. Similarly, the term "(lower)alkoxy" means an alkoxy group in which the alkyl portion is straight or branched and contains from 1 to 6 carbon atoms.

For therapeutic use, the pharmacologically active compounds of this invention will normally be administered as a pharmaceutical composition comprising as the (or an) essential active ingredient at least one such compound in the basic form or in the form of a nontoxic pharmaceutically acceptable acid addition salt, in association with a pharmaceutically acceptable carrier.

The pharmaceutical compositions may be administered orally, parenterally or by rectal suppository. A wide variety of pharmaceutical forms may be employed. Thus, if a solid carrier is used, the preparation may be tableted, placed in a hard gelatin capsule in powder or pellet form, or in the form of a troche or lozenge. If a liquid carrier is employed, the preparation may be in the form of a syrup, emulsion, soft gelatin capsule, sterile solution for injection, or an aqueous or non-aqueous liquid suspension. The pharmaceutical compositions are prepared by conventional techniques appropriate to the desired preparation.

Preferably, each dosage unit will contain the active ingredient in an amount of from about 50 mg. to about 250 mg., and most preferably from about 100 mg. to about 200 mg. The active ingredient will preferably be administered in equal doses from two to four times a day. The daily dosage regimen will preferably be from 250 mg. to about 1000 mg., and most preferably from about 500 mg. to about 750 mg.

Histamine $H_2$-receptor antagonists have been shown to be effective inhibitors of gastric secretion in animals and man, Brimblecombe et al., *J. Int. Med. Res.*, 3, 86 (1975). Clinical evaluation of the histamine $H_2$-receptor antagonist cimetidine has shown it to be an effective therapeutic agent in the treatment of peptic ulcer disease, Gray et al., *Lancet*, 1, 8001 (1977). The compounds prepared in Examples 1 (BL-6040) and 4 (BL-6044) have been compared with cimetidine in two standard tests. BL-6040 and BL-6044 have been found to be more potent than cimetidine as a histamine $H_2$-receptor antagonist in isolated guinea pig atria (in vitro) and more potent than cimetidine as an inhibitor of gastric acid secretion in rats (in vivo).

Histamine $H_2$-Receptor Antagonism-Isolated Guinea Pig Atria Assay

Histamine produces concentration-related increases in the contractile rate of isolated, spontaneously beating guinea pig right atria. Black et al., *Nature*, 236, 385 (1972, described the receptors involved in this effect of histamine as histamine $H_2$-receptors when they reported the properties of burimamide, a competitive antagonist of these receptors. Subsequent investigations by Hughes and Coret, *Proc. Soc. Exp. Biol. Med.* 148, 127 (1975) and Verma and McNeill, *J. Pharmacol. Exp. Ther.*, 200, 352 (1977) support the conclusion of Black and coworkers that the positive chronotropic effect of histamine in isolated guinea pig right atria is mediated via histamine $H_2$-receptors. Black et al., *Agents and Actions*, 3, 133 (1973) and Brimblecombe et al., *Fed. Proc.*, 35, 1931 (1976) have utilized isolated guinea pig right atria as a means for comparing the activities of histamine $H_2$-receptor antagonists. The present comparative studies were carried out using a modification of the procedure reported by Reinhardt et al., *Agents and Actions*, 4, 217 (1974).

Male Hartley strain guinea pigs (350–450 gm.) were sacrificed by a blow on the head. The heart was excised and placed in a Petri dish of oxygenated (95% $O_2$, 5% $CO_2$) modified Krebs solution (g./liter: NaCl 6.6, KCl 0.35, $MgSO_4.7 H_2O$ 0.295, $KH_2PO_4$ 0.162, $CaCl_2$ 0.238, NaHCO₃ 2.1 and dextrose 2.09). The spontaneously beating right atrium was dissected free from other tissues and a silk thread (4-0) attached to each end. The atrium was suspended in a 20 ml. muscle chamber containing oxygenated modified Krebs solution maintained at 32° C. Atrial contractions were recorded isometrically by means of a Grass FT 0.03 force displacement transducer and recordings of contractile force and rate were made with Beckman RP Dynograph.

A resting tension of 1 g. was applied to the atrium and it was allowed to equilibrate for 1 hour. At the end of the equilibration period a submaximal concentration of histamine dihydrochloride (3 to $10^{-6}$ M) was added to the bath and washed out to prime the tissue. Histamine was then added to the bath in a cumulative fashion using ½ log 10 intervals to give final molar bath concentrations of $1 \times 10^{-7}$ to $3 \times 10^{-5}$. The histamine-induced increase in atrial rate was allowed to plateau before the next successive concentration was added. The maximal response invariably occurred at the $3 \times 10^{-5}$ M concentration. The histamine was washed out several times and the atrium allowed to return to control rate. The test compound ($3 \times 10^{-5}$ M) was then added and after a 30 minute incubation the histamine concentration-response was repeated adding higher concentrations as needed.

The histamine ED50 values (concentration of histamine which increased contractile rate 50% of maximum) and 95% confidence limits before and after the test compound were obtained by regression analysis as described by Finney, *Probit Analysis*, 3rd ed., Cambridge (1971). Concentration-response curve displacement factors were calculated as follows:

$$\text{Displacement factor} = \frac{ED50 \text{ Histamine } + \text{ Compound}}{ED50 \text{ Histamine Alone}}$$

The factors obtained for BL-6040 and BL-6044 were then expressed as ratios of the factor obtained for cimetidine.

$$\text{Activity Ratio} = \frac{\text{Test Compound Displacement Factor} - 1}{\text{Cimetidine Displacement Factor} - 1}$$

The results obtained from these studies are summarized in Table 1. Cimetidine, BL-6040 and BL-6044 displaced the histamine-response curve to the right by factors of 25.26, 46.20 and 43.18, respectively. Based on the concentration-response curve displacement factors, BL-6040 was about 1.86 times as active as cimetidine and BL-6044 about 1.74 times as active as cimetidine as a histamine H₂-receptor antagonist in isolated guinea pig right atria.

Table 1

| Relative Activity of Cimetidine, BL-6040 and BL-6044 in Isolated Guinea Pig Atria. | | | | | |
|---|---|---|---|---|---|
| Compound | N | Concentration | Histamine ED50 With 95% Confidence Limits (µg/ml) | Concentration-Response Curve Displacement Factor | Activity Ratio Relative to Cimetidine |
| Histamine Control | 8 | — | 0.19 (0.15–0.24) | — | — |
| Cimetidine | 8 | $3 \times 10^{-5}$M | 4.80 (3.9–5.9) | 25.26 | 1.0 |
| Histamine Control | 2 | — | 0.45 (0.32–0.63) | — | — |
| BL-6040 | 2 | $3 \times 10^{-5}$M | 20.79 (19.99–21.63) | 46.20 | 1.86 |
| Histamine Control | 2 | — | 0.33 (0.27–0.40) | — | — |
| BL-6044 | 2 | $3 \times 10^{-5}$M | 14.25 (13.10–15.50) | 43.18 | 1.74 |

N = Number of experiments

Determination of Gastric Antisecretory Activity in the Two Hour Pylorus Ligated (Shay) Rat The pyloric ligation procedure in the rat was designed by Shay et al., *Gastroenterology*, 5, 53 (1945) for the study of perforating gastric ulcers; however, as the method became known, it was also employed as a means of studing rat gastric secretion, Shay et al., *Gastroenterology*, 26, 906 (1954), Brodie, D. A., *Am. J. Dig. Dis.*, 11, 231 (1966). A modification of this procedure is presently used to evaluate compounds for gastric antisecretory activity.

Male Long Evans rats, 280–300 gm., are used. The animals are placed in individual cages and fasted for 24 hours with free access to water. Under ether anesthesia, the stomach is reached through a midline incision, and a cotton-thread ligature is placed around the pylorus. After wound closure, ether administration is stopped and either cimetidine, BL-6040, BL-6044 or vehicle is administered intraperitoneally in a volume of 1 mg./kg. All compounds are solubilized with one equivalent of HCl and brought to the proper volume with water. The animals are returned to their cages from which the water bottles have been removed and two hours later are sacrificed with ether. The stomach is removed and the two hour gastric collection is drained into a graduated test tube for volume determination. Titratable acidity is measured by titrating a one ml. sample to pH 7.0 with 0.02 NaOH, using an Autoburet and electrometric pH meter (Radiometer). Titratable acid output is calculated in microequivalents by mutiplying the volume in milliliters by the acid concentration in milliequivalents per liter. The percent inhibition of acid output is calculated as follows % Inhibition Acid Output =

$$\frac{\text{Acid Output-Control} - \text{Acid Output-Drug}}{\text{Acid Output-Control}} \times 100$$

The test results are summarized in Table 2. These results indicate that, in the two hour pylorus ligated rat preparation, BL-6040 is 2.93 times more potent and BL-6044 is 2.11 times more potent than cimetidine with respect to the inhibition of gastric acid output.

Table 2
Effect of BL-6040, BL-6044 and Cimetidine on Gastric Acid Output in the Two Hour Pylorus Ligated Rat.

| Compound | Dose (ip) μMole/kg | Percent Inhibition Acid Output | ED50 μMole/kg | Potency Ratio |
|---|---|---|---|---|
| BL-6040 | 20 | 80 | 4.11 | 2.93 |
|  | 10 | 69 | (1.76–7.60) | (1.1–12.4) |
|  | 5 | 53 |  |  |
| BL-6044 | 20 | 73 | 5.73 | 2.11 |
|  | 10 | 58 | (1.81–7.60) | (0.63–10.9) |
|  | 5 | 52 |  |  |
| Cimetidine | 20 | 76 | 12.1 | 1.0 |
|  | 10 | 45 | (5.49–33.4) |  |
|  | 5 | 26 |  |  |

5–20 animals were employed at each dose.

DESCRIPTION OF THE PREFERRED EMBODIMENTS

EXAMPLE 1

1-Nitro-2-(2-propynylamino)-2-{2-[(thiazol-2-yl)methylthio]ethylamino}ethylene (BL-6040)

A mixture of 1-nitro-2-methylthio-2-{2-[(thiazol-2-yl)methylthio]ethylamino}ethylene [prepared according to the procedure described in U.S. Pat. No. 4,046,907] (2.54 g; 8.71 mmoles) and propargylamine (5.08 ml) in acetonitrile (30 ml) was stirred and heated to reflux temperature under a positive pressure of nitrogen for 5 hours then stirred at ambient temperature for 11 hours. The reaction mixture was filtered and 1.12 g of product was collected. Recrystallization from isopropanol gave the title compound mp 121°–123°.

Anal. Calcd for $C_{11}H_{14}N_4O_2S_2$: C, 44.28; H, 4.73, N, 18.78; S, 21.49. Found: C, 44.51; H, 4.63; N, 18.72; S, 21.31.

EXAMPLE 2

1-Nitro-2-(2-propynylamino)-2-{2-[(thiazol-2-yl)methylthio]ethylamino}ethylene (BL-6040)

A. A solution of propargylamine (1.10 g, 0.02 mole) in 22 ml of methanol was added dropwise to a stirred suspension of 1-methylsulfinyl-1-methylthio-2-nitroethylene at 25°. After 1 hour at ambient temperature, the solution was evaporated under reduced pressure, triturated under 20 ml of cold isopropanol and filtered to give product. Recrystallization from isopropanol gave 1-methylthio-1-(2-propynylamino)-2-nitroethylene; mp 131°–132°.

Anal. Calcd for $C_6H_8N_2O_2S$: C, 41.85; H, 4.68; N, 16.27 S, 18.62. Found: C, 41.64; H, 4.52; N, 16.66; S, 18.65.

B. A solution of the product of Step A is treated with about an equimolar amount of 2-[(thiazol-2-yl)methylthio]ethylamine to produce, after workup, the title product.

EXAMPLE 3

1-Nitro-2-(propynylamino)-2-{2-[(thiazol-2-yl)methylthio]ethylamino}ethylene (BL-6040)

A. A solution of the product of Step A of Example 2 is reacted with about an equimolar amount of cysteamine hydrochloride and about one equivalent of base, to produce 1-nitro-2-(2-propynylamino)-2-(2-mercaptoethyl)ethylene.

B. The product of Step A is reacted in a non-reactive solvent with about an equimolar amount of 2-chloromethylthiazole and about one equivalent of base, and the title product is thereby produced.

EXAMPLE 4

N-Cyano-N'-(2-propyn-1-yl)-N''-{2-[(thiazol-2-yl)methylthio]ethyl}guanidine (BL-6044)

A mixture of N-cyano-N'-{2-[(thiazol-2-yl)methylthio]ethyl}-S-methylisothiourea [prepared according to the procedure described in U.S. Pat. No. 3,950,333] (4.40 g, 16.1 mmole) and propargylamine (8.8 ml) in methanol (35 ml) was stirred and heated to reflux temperature under a positive pressure of nitrogen for 16 hours. The reaction mixture was evaporated under reduced pressure, the residue dissolved in warm isopropanol, and then cooled and filtered to yield 2.26 g of product. Recrystallization from isopropanol with Darco treatment gave the title compound; mp 137.5°–139.5°.

Anal. Calcd for $C_{11}H_{13}N_5S_2$: C, 47.29; H, 4.69; N, 25.07; S, 22.95. Found: C, 47.37; H, 4.60; N, 25.43; S, 23.19.

EXAMPLE 5

N-Cyano-N'-(2-propyn-1-yl)-N''-{2-[(thiazol-2-yl)methylthio]ethyl}guanidine (BL-6044)

A. A solution of dimethyl cyanodithioimidocarbonate (16.0 g; 0.109 mole) and propargylamine (6.03 g, 0.109 mole) in acetonitrile (320 ml) was stirred at reflux for 4 hours, then at ambient temperature for 12 hours. Workup gave 13.58 g (85%) of N-cyano-N'-(2-propyn-1-yl)-S-methylisothiourea; mp 160°–164°.

B. The product of Step A is reacted with about an equimolar amount of 2-[(thiazol-2-yl)methylthio]ethylamine to give, after workup, the title product.

EXAMPLE 6

N-Cyano-N'-(2-propyn-1-yl)-N''-{2-(thiazol-2-yl)methylthio]ethyl}guanidine (BL-6044)

A. A mixture of the product of Step A of Example 5 (1.53 g; 10 mmoles), cysteamine hydrochloride (1.136 g; 10 mmoles) and 0.055 g of hydroquinone in 10 ml of dimethylformamide is slightly warmed to dissolve. To this solution is added 10 ml of 1 N aqueous sodium hydroxide and nitrogen is bubbled through the solution. After standing at room temperature for 17 hours, the reaction mixture is evaporated to dryness to give a mixture of the desired product and sodium chloride. The N-cyano-N'-(2-propyn-1-yl)-N''-(2-mercaptoethyl)guanidine is extracted from the mixture with 10 ml of ethanol and the ethanolic solution is used in Step B below.

B. The ethanolic solution of the product of Step A is reacted with about an equimolar amount of 2-chloromethylthiazole and about one equivalent of base, and the title product is thereby produced.

EXAMPLE 7

The general procedure of Example 1 is repeated, except that the propargylamine utilized therein is replaced by an equimolar amount of 2-butyn-1-amine,
3-butyn-1-amine,
4-pentyn-1-amine,
3-amino-1-butyne and
1,1-dimethylpropargylamine, respectively,
and there is thereby produced
1-nitro-2-(2-butyn-1-ylamino)-2-{2-[(thiazol-2-yl)methylthio]ethylamino}ethylene,
1-nitro-2-(3-butyn-1-ylamino)-2-{2-[(thiazol-2-yl)methylthio]ethylamino}ethylene,
1-nitro-2-(4-pentyn-1-ylamino)-2-{2-[(thiazol-2-yl)methylthio]ethylamino}ethylene,
1-nitro-2-(3-butyn-2-ylamino)-2-{2-[(thiazol-2-yl)methylthio]ethylamino}ethylene and
1-nitro-2-(2-methyl-3-butyn-2-ylamino)-2-{2-[(thiazol-2-yl)methylthio]ethylamino}ethylene, respectively.

EXAMPLE 8

The general procedure of Example 4 is repeated, except that the propargylamine utilized therein is replaced by an equimolar amount of 2-butyn-1-amine,
3-butyn-1-amine,
4-pentyn-1-amine,
3-amino-1-butyne and
1,1-dimethylpropargylamine, respectively,
and thereby produced
N-cyano-N'-(2-butyn-1-yl)-N"-{2-[(thiazol-2-yl)methylthio]ethyl}guanidine,
N-cyano-N'-(3-butyn-1-yl)-N"-{-2-[(thiazol-2-yl)methylthio]ethyl}guanidine,
N-cyano-N'-(4-pentyn-1-yl)-N"-{2-[(thiazol-2-yl)methylthio]ethyl}guanidine,
N-cyano-N'-(3-butyn-2-yl)-N"-{-2-[(thiazol-2-yl)methylthio]ethyl}guanidine and
N-cyano-N'-(2-methyl-3-butyn-2-yl)-N"-{2-[(thiazol-2-yl)methylthio]ethyl}guanidine, respectively.

EXAMPLE 9

1-Nitro-2-(2-propynylamino)-2-{3-[(thiazol-2-yl)methylthio]propylamino}ethylene

When 2-hydroxymethylthiazole is reacted with 3-mercaptopropylamine hydrochloride [prepared according to the procedure described in *J. Org. Chem.*, 27, 2846 (1962)] in aqueous hydrobromic acid (48%) and the resultant amine successively treated with 1,1-bis(methylthio)-2-nitroethylene and excess propargylamine, the title compound is produced.

EXAMPLE 10

N-Cyano-N'-(2-propyn-1-yl)-N"-{3-[(thiazol-2-yl)methylthio]propyl}guanidine

Reaction of 3-[(thiazol-2-yl)methylthio]propylamine with dimethyl cyanodithioimidocarbonate and treatment of the product with excess propargylamine yields the title compound.

EXAMPLE 11

1-Cyano-2-(2-propynylamino)-2-{2-[(thiazol-2-yl)methylthio]ethylamino}ethylene

When 2-[(thiazol-2-yl)methylthio]ethylamine is reacted in an inert solvent with about an equimolar amount of 1-cyano-2-ethoxy-2-propynylaminoethylene [prepared from propargylamine and 1-cyano-2,2-bis(ethoxy)ethylene, which is itself prepared according to the procedure described in *J. Am. Chem. Soc.*, 71, 47 (1949)], the title product is produced.

EXAMPLE 12

1-Cyano-2-(2-propynylamino)-2-{2-[(thiazol-2-yl)methylthio]ethylamino}ethylene

When 2-[(thiazol-2-yl)methylthio]ethylamine is reacted with 1-cyano-2,2-bis(methoxy)ethylene [prepared according to the procedure described in *J. Chem. Soc.*, (Suppl. Issue No. 1), S106-111 (1949)] and the resultant 1-cyano-2-methoxy-2-{2-[(thiazol-2-yl)methylthio]ethylamino}ethylene is reacted with propargylamine in the procedure of Example 1, the title compound is produced.

EXAMPLE 13

When N-phenylsulfonylimidodithiocarbonic acid dimethyl ester [prepared according to the general procedure described in *Chem. Ber.*, 99, 2885 (1966)] is reacted in an inert solvent with 2-[(thiazol-2-yl)methylthio]ethylamine and then with excess propargylamine according to the procedure of Example 2, there is produced N-phenylsulfonyl-N'-(2-propyn-1-yl)-N"-{2-[(thiazol-2-yl)methylthio]ethyl}guanidine.

When the above procedure is repeated, except that the N-phenylsulfonylimidodithiocarbonic acid dimethyl ester utilized therein is replaced by an equimolar amount of N-(4-chlorophenylsulfonyl)imidodithiocarbonic acid dimethyl ester,
N-(4-methylphenylsulfonyl)imidodithiocarbonic acid dimethyl ester,
N-(3,4-dichlorophenylsulfonyl)imidodithiocarbonic acid dimethyl ester and
N-methylsulfonylimidodithiocarbonic acid dimethyl ester, respectively,

[each prepared according to the general procedure described in *Chem. Ber.*, 99, 2885 (1966)], there is thereby produced
N-(4-chlorophenylsulfonyl)-N'-(2-propyn-1-yl)-N"-{2-[(thiazol-2-yl)methylthio]ethyl}guanidine,
N-(4-methylphenylsulfonyl)-N'-(2-propyn-1-yl)-N"-{2-[(thiazol-2-yl)methylthio]ethyl}guanidine,
N-(3,4-dichlorophenylsulfonyl)-N'-(2-propyn-1-yl)-N"-{2-[(thiazol-2-yl)methylthio]ethyl}guanidine and
N-methylsulfonyl-N'-(2-propyn-1-yl)-N"-{2-[(thiazol-2-yl)methylthio]ethyl}guanidine, respectively.

EXAMPLE 14

The reaction of methyl phenyl sulfone with carbon disulfide under strongly basic conditions and treatment with methyl iodide according to the general procedure of *Bull. Soc. Chim. Fr.*, 637 (1973), yields 1-phenylsulfonyl-2,2-bis(methylthio)ethylene. When 1-phenylsulfonyl-2,2-bis(methylthio)ethylene is reacted with 2-[(thiazol-2-yl)methylthio]ethylamine and then with propargylamine according to the procedure of Example 1, there is produced 1-phenylsulfonyl-2-(propynylamino)-2-{2-[(thiazol-2-yl)methylthio]ethylamino}ethylene.

When the above procedure is repeated, except that the methyl phenyl sulfone utilized therein is replaced by an equimolar amount of 4-chlorophenyl methyl sulfone,
3,4-dichlorophenyl methyl sulfone,
4-methylphenyl methyl sulfone and dimethyl sulfone, respectively, there is thereby produced
1-(4-chlorophenylsulfonyl)-2-(2-propynylamino)-2-{2-[(thiazol-2-yl)methylthio]ethylamino}ethylene,
1-(3,4-dichlorophenylsulfonyl)-2-(2-propynylamino)-2-{2-[(thiazol-2-yl)methylthio]ethylamino}ethylene,
1-(4-methylphenylsulfonyl)-2-(propynylamino)-2-{2-[(thiazol-2-yl)methylthio]ethylamino}ethylene and
1-methylsulfonyl-2-(2-propynylamino)-2-{2-[(thiazol-2-yl)methylthio]ethylamino}ethylene, respectively.

EXAMPLE 15

When 2-chloromethyl-4-methylthiazole [prepared by the reaction of thionyl chloride and 2-hydroxymethyl-4-methylthiazole, which itself is prepared according to the procedure of *J. Chem. Soc.*, (Suppl. Issue No. 1), S106-111 (1966) or *Acta Chem. Scand.*, 20, 2649 (1966)] is reacted with cysteamine hydrochloride and about two equivalents of a strong base such as sodium methoxide, and the resultant amine is treated with 1,1-bis(methylthio)-2-nitroethylene, there is produced 1-nitro-2-methylthio-2-{2-[(4-methylthiazol-2-yl)methylthio]ethylamino}ethylene. When the latter compound is reacted with propargylamine according to the general procedure of Example 1, there is produced 1-nitro-2-(2-propynylamino)-2-{2-[(4-methylthiazol-2-yl)methylthio]ethylamino}ethylene.

When the above procedure is repeated, except that the 2-chloromethyl-4-methylthiazole utilized therein is replaced by an equimolar amount of the chloromethylthiazoles prepared by reacting thionyl chloride with 2-hydroxymethyl-4,5-dimethylthiazole,
4-hydroxymethyl-2-methylthiazole,
5-hydroxymethyl-2-methylthiazole,
5-hydroxymethyl-4-methylthiazole and
4-hydroxymethylthiazole, respectively,
[which are prepared by the procedures described in *Helv. Chim. Acta*, 31, 652 (1948); *Zh Obshch. Khim.*, 32, 570 (1962) (C.A., 58, 2525b, 1963); *J. Am. Chem. Soc.*, 67, 400 (1945); and *Zh. Obshch. Khim.*, 27, 726 (1957) (C.A., 51, 16436h, 1957), respectively], there is thereby produced
1-nitro-2-(propynylamino)-2-{2-[(4,5-dimethylthiazol-2-ylmethylthio]ethylamino}ethylene,
1-nitro-2-(2-propynylamino)-2-{2-[(2-methylthiazol-4-yl)methylthio]ethylamino}ethylene,
1-nitro-2-(2-propynylamino)-2-{2-[(2-methylthiazol-5-yl)methylthio]ethylamino}ethylene,
1-nitro-2-(2-propynylamino)-2-{2-[(4-methylthiazol-5-yl)methylthio]ethylamino}ethylene and
1-nitro-2-(2-propynylamino)-2-{2-[(thiazol-4-yl)methylthio]ethylamino}ethylene, respectively.

EXAMPLE 16

When 2-chloromethyl-4-methylthiazole [prepared from 2-hydroxymethyl-4-methylthiazole and thionyl chloride] is reacted with cysteamine hydrochloride and about two equivalents of a strong base such as sodium methoxide and the resultant amine treated with dimethyl cyanodithioimidocarbonate there is produced N-cyano-N'-{2-[(4-methylthiazol-2-yl)methylthio]ethyl}-S-methylisothiourea. When the latter compound is reacted with propargylamine according to the general procedure of Example 4, there is produced N-cyano-N'-(2-propyn-1-yl)-N''-{2-[(4-methylthiazol-2-yl)methylthio]ethyl}guanidine.

When the above procedure is repeated, except that the 2-chloromethyl-4-methylthiazole utilized therein is replaced by an equimolar amount of the chloromethylthiazoles prepared by reacting thionyl chloride with 2-hydroxymethyl-4,5-dimethylthiazole,
4-hydroxymethyl-2-methylthiazole,
5-hydroxymethyl-2-methylthiazole,
5-hydroxymethyl-4-methylthiazole and
4-hydroxymethylthiazole, respectively, there is thereby produced
N-cyano-N'-(2-propyn-1-yl)-N''-{2-[(4,5-dimethylthiazole-2-yl)methylthio]ethyl}guanidine,
N-cyano-N'-(2-propyn-1-yl)-N''-{2-[(2-methylthiazol-4-yl)methylthio]ethyl}guanidine,
N-cyano-N'-(2-propyn-1-yl)-N''-{2-[(2-methylthiazol-5-yl)methylthio]ethyl}guanidine,
N-cyano-N'-(2-propyn-1-yl)-N''-{2-[(4-methylthiazol-5-yl)methylthio]ethyl}guanidine and
N-cyano-N'-(2-propyn-1-yl)-N''-{2-[(thiazol-4-yl)methylthio]ethyl}guanidine, respectively.

EXAMPLE 17

1-Nitro-2-(2-propynylamino)-2-{2-[(4-dimethylaminomethylthiazol-2-yl)methylthio]ethylamino}ethylene When 2-bromo-4-chloromethylthiazole [prepared according to the procedure described in *Rev. Roumaine Chim.*, 10, 897 (1965) (C. A., 64, 8164b 1966)] is reacted with an ethanol solution of dimethylamine and the resultant 2-bromo-4-dimethylaminomethylthiazole is treated with a strong base and formaldehyde according to the general procedure described in *Acta Chem. Scand.*, 20, 2649 (1966) there is produced 4-dimethylaminomethyl-2-hydroxymethylthiazole. When that compound is reacted with thionyl chloride to produce 2-chloromethyl-4-dimethylaminomethylthiazole, and the latter compound is reacted according to the general procedure of Example 15, the title compound is thereby produced.

EXAMPLE 18

The general procedure of Example 17 is repeated, except that the dimethylamine utilized therein is replaced by an equimolar amount of diethylamine,
N-methylethylamine and
N-methylaniline, respectively,
and there is thereby produced
1-nitro-2-(2-propynylamino)-2-{2-[(4-diethylaminomethylthiazol-2-yl)methylthio]ethylamino}ethylene,
1-nitro-2-(2-propynylamino)-2-{2-[(4-{[N-ethyl-N-methylamino]methyl}thiazol-2-yl)ethylamino]ethylene and
1-nitro-2-(2-propynylamino)-2-{2-[(4-{[N-methyl-N-phenylamino]methyl}thiazol-2-yl)ethylamino}ethylene, respectively.

EXAMPLE 19

N-Cyano-N'-(2-propyn-1-yl)-N''-{2-[(4-dimethylaminomethylthiazol-2-yl)methylthio]ethyl}guanidine When 4-dimethylaminomethyl-2-hydroxymethylthiazole prepared in Example 17 is reacted with thionyl chloride, and the resulting 2-chloromethyl-4-dimethylaminomethylthiazole is reacted according to the general procedure of Example 16, the title compound is produced.

EXAMPLE 20

When 2-bromo-4-chloromethylthiazole is reacted with an ethanol solution of
diethylamine,
N-methylethylamine and
N-methylaniline, respectively,
there is thereby produced
2-bromo-4-diethylaminomethylthiazole,
2-bromo-4-[(N-ethyl-N-methyl)aminomethyl]thiazole and
2-bromo-4-[(N-methyl-N-phenyl)aminomethyl]thiazole, respectively.

When the latter compounds are treated with a strong base and formaldehyde according to the general procedure described in *Acta Chem. Scand.*, 20, 2649 (1966), and the resulting 2-hydroxymethyl derivatives are reacted with thionyl chloride, there is thereby produced
2-chloromethyl-4-diethylaminomethylthiazole,
2-chloromethyl-4-[(N-ethyl-N-methyl)aminomethyl]thiazole and
2-chloromethyl-4-[(N-ethyl-N-phenyl)aminomethyl]thiazole, respectively.

When these three compounds are reacted according to the general procedure of Example 16, there is thereby produced N-cyano-N'-(2-propyn-1-yl)-N''-{2-[(4-diethylaminomethylthiazol-2-yl)methylthio]ethyl}-guanidine,
N-cyano-N'-(2-propyn-1-yl)-N''-{2-[(4-{[N-ethyl-N-methyl]aminomethyl}thiazole-2-yl)methylthio]ethyl}guanidine and N-cyano-N'-(2-propyn-1-yl)-N''-{2-[(4-{[N-methyl-N-phenyl]aminomethyl}thiazole-2-yl)methylthio]ethyl}guanidine, respectively.

EXAMPLE 21

1-Nitro-2-(2-propynylamino)-2-{2-[(2guanidinothiazol-4-yl)methylthio]ethylamino]ethylamino}ethylene (BL-6117)

When a solution of 1-nitro-2-(2-propynylamino)-2-(2-merceptoethyl)ethylene [prepared in Step A of Example 3] is reacted with about an equimolar amount of 2-guanidino-4-chloromethylthiazole hydrochloride [prepared according to the procedure described in South Africa Pat. No. 78/2129] and about two equivalents of base, the title product is produced.

EXAMPLE 22

N-Cyano-N'-(2-propyn-1-yl)-N''-{2-[(2-guanidinothiazol-4-yl)methylthio]ethyl}guanidine (BL-6116)

When an ethanolic solution of N-cyano-N'-(2-propyn-1-yl)-N''-(2-mercaptoethyl)guanidine [prepared in Step A of Example 6] is reacted with about an equimolar amount of 2-guanidino-4-chloromethylthiazle hydrochloride and about two equivalents of base, the title product is produced.

EXAMPLE 23

N-Cyano-N'-(2-propyn-1-yl)-N''-{2-[(2-guanidinothiazol-4-yl)methylthio]ethyl}guanidine (BL-6116)

A mixture of N-cyano-N'-{2-[(2-guanidinothiazol-4-yl)methylthio]ethyl}-S-methylisothiourea [prepared according to the procedure described in South Africa Pat. No. 78/2129] (3.0 g; 9.11 mmoles) and propargylamine (6.0 ml) in methanol (15 ml) was stirred and heated at reflux temperature under a positive pressure of nitrogen for 20 hours. The reaction mixture was evaporated under reduced pressure and the residue triturated with isopropanol and filtered to give product (1.5 g). Recrystallization from nitromethane gave the title compound, mp 146°–148°.

EXAMPLE 24

1-Nitro-2-(2-propynylamino)-2-{2-[(2-guanidinothiazol-4-yl)methylthio]ethylamino}ethylene (BL-6117)

A. A solution of 2-[(2-guanidinothiazol-4-yl)methylthio]ethylamine (from the dihydrochloride, 20.0 g; 66.0 mmoles) [prepared according to the procedure described in South Africa Pat. No. 78/2129] and 1,1-bis(-methylthio)-2-nitroethylene [prepared according to the procedure described in *Chem. Ber.*, 100, 591 (1967) or *Acta Chem. Scand.*, 21 2797 (1967)] (10.9 g; 66.0 mmoles) in isopropanol (600 ml) was stirred at ambient temperature under a positive pressure of nitrogen for 2 hours, at reflux temperature for 1 hour and then at ambient temperature for 54 hours. The reaction mixture was cooled and filtered to give 15.8 g of 1-nitro-2-methylthio-2-{2-[(2-guanidinothiazol-4-yl)methylthio]ethylamino}ethylene as a yellow solid, mp 151°–156°, which was used without further purification in Step B below.

B. A mixture of the product of Step A (3.0 g; 8.61 mmoles) and propargylamine (6.0 ml) in acetonitrile (21 ml) was stirred and heated at reflux temperature under a positive pressure of nitrogen for 18 hours. The reaction mixture was evaporated under reduced pressure and the residue was placed on 70 g of silica gel and chromatographed using a gradient elution of methylene chloride-methanol. The appropriate fractions were combined and evaporated, and the 480 mg of product was recrystallized from isopropanol to yield the title compound containing approximately ⅔ mole of isopropanol, mp 82°–90°. Thin layer chromatography on silica, using methylene chloride:methanol (90:10), gave Rf 0.25.

EXAMPLE 25

N-Cyano-N'-(2-propyn-1-yl)-N''-{2-[(2-guanidinothiazol-4-yl]methylthio]ethyl≡guanidine (BL-6116)

N-Cyano-N'-(2-propyn-1-yl)-S-methylisothiourea (prepared in Example 5, Step A, above) is reacted in an inert solvent with about an equimolar amount of 2-[(2-guanidinothiazol-4-yl)methylthio]ethylamine to produce, after workup, the title product.

EXAMPLE 26

1-Nitro-2-(2-propynylamino)-2-{2-[(2-guanidinothiazol-4-yl)methylthio]ethylamino}ethylene (BL-6117)

1-Methylthio-1-(2-propynylamino)-2-nitroethylene (prepared in Example 2, Step A, above) is reacted in an inert solvent with about an equimolar amount of 2-[(2-guanidinothiazol-4-yl)methylthio]ethylamine to produce, after workup, the title product.

We claim:

1. A compound of the formula

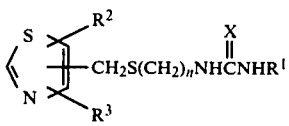

wherein $R^1$ is a straight or branched chain alkynyl group containing from 3 to 9 carbon atoms, inclusive; $R^2$ and $R^3$ each are independently hydrogen, (lower)alkyl, guanidino or $-(CH_2)_pNR^4R^5$; $R^4$ and $R^5$ each are independently hydrogen, (lower)alkyl or phenyl; n is 2 or 3; p is 1, 2 or 3; X is $NR^6$ or $CHR^6$; $R^6$ is cyano, nitro, $SO_2Ar$ or $SO_2$(lower)alkyl; and Ar is phenyl or phenyl containing 1 or 2 substituents selected from halogen and (lower)alkyl; or a nontoxic, pharmaceutically acceptable salt thereof.

2. A compound of claim 1 having the formula

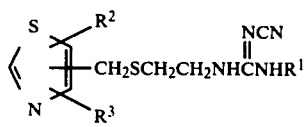

wherein $R^1$, $R^2$ and $R^3$ are as defined above, or a nontoxic, pharmaceutically acceptable salt thereof.

3. A compound of claim 1 having the formula

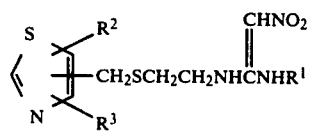

wherein $R^1$, $R^2$ and $R^3$ are as defined above, or a nontoxic, pharmaceutically acceptable salt thereof.

4. A compound of claim 1 having the formula

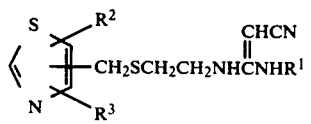

wherein $R^1$, $R^2$ and $R^3$ are as defined above, or a nontoxic, pharmaceutically acceptable salt thereof.

5. A compound of claim 1 having the formula

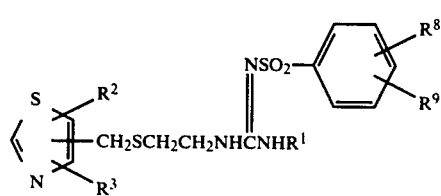

wherein $R^1$, $R^2$ and $R^3$ are as defined above, and $R^8$ and $R^9$ each are independently hydrogen, halogen or (lower)alkyl, or a nontoxic, pharmaceutically acceptable salt thereof.

6. A compound of claim 1 having the formula

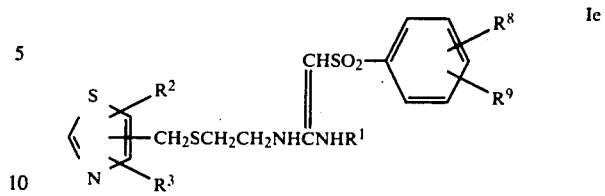

wherein $R^1$, $R^2$ and $R^3$ are as defined above, and $R^8$ and $R^9$ each are independently hydrogen, halogen or (lower)alkyl, or a nontoxic, pharmaceutically acceptable salt thereof.

7. A compound of the formula

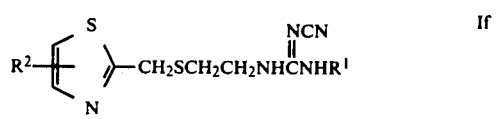

wherein $R^1$ and $R^2$ are as defined above, or a nontoxic, pharmaceutically salt thereof.

8. A compound of the formula

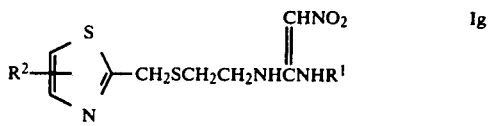

wherein $R^1$ and $R^2$ are as defined above, or a nontoxic, pharmaceutically acceptable salt thereof.

9. A compound of claim 7 having the formula

wherein m is an integer of from 1 to 6, inclusive; and $R^{10}$ is hydrogen or methyl; or a nontoxic, pharmaceutically acceptable salt thereof.

10. A compound of claim 8 having the formula

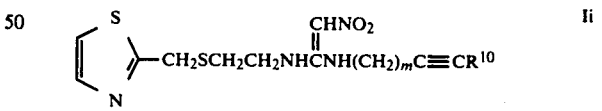

wherein m is an integer of from 1 to 6, inclusive; and $R^{10}$ is hydrogen or methyl; or a nontoxic, pharmaceutically acceptable salt thereof.

11. A compound of claim 7 having the formula

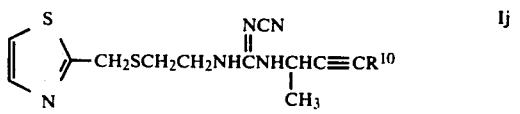

wherein $R^{10}$ is hydrogen or methyl; or a nontoxic, pharmaceutically acceptable salt thereof.

12. A compound of claim 8 having the formula

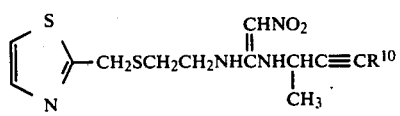
Ik wherein $R^{10}$ is hydrogen or methyl, or a nontoxic, pharmaceutically acceptable salt thereof.

13. The compound of the formula

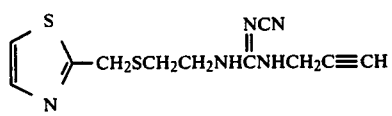
Im or a nontoxic, pharmaceutically acceptable salt thereof.

14. The compound of the formula

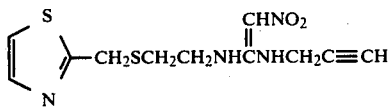
In or a nontoxic, pharmaceutically acceptable salt thereof.

15. The compound of the formula

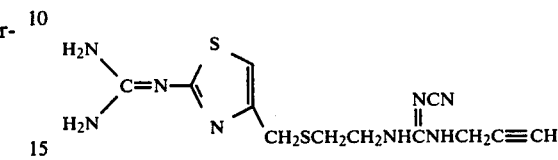
Io or a nontoxic, pharmaceutically acceptable salt thereof.

16. The compound of the formula

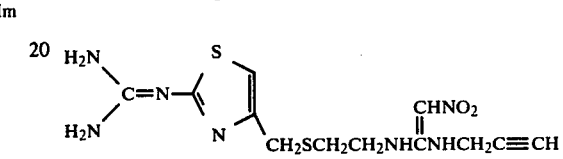
Ip or a nontoxic, pharmaceutically acceptable salt thereof.

* * * * *

UNITED STATES PATENT AND TRADEMARK OFFICE
CERTIFICATE OF CORRECTION

PATENT NO. : 4,200,578

DATED : April 29, 1980

INVENTOR(S) : Aldo A. Algieri et al.

It is certified that error appears in the above-identified patent and that said Letters Patent are hereby corrected as shown below:

In Column 1, Line 22 thereof, "reeceptors" should read -- receptors --.

In Column 2, Line 4 thereof, "trifloroethyl" should read -- trifluoroethyl --.

In Column 3, Line 56 thereof, "seperated" should read -- separated --.

In Column 3, Line 59 thereof, "seperated" should read -- separated --.

In Column 3, Line 62 thereof, "seperated" should read -- separated --.

In Column 10, Line 32 thereof, "or at" should read -- at or --.

In Column 10, at Line 50, the product (XII) of the first part of Scheme VI, presently shown as

UNITED STATES PATENT AND TRADEMARK OFFICE
CERTIFICATE OF CORRECTION

PATENT NO. : 4,200,578

DATED : April 29, 1980

INVENTOR(S) : Aldo A. Algieri et al.

It is certified that error appears in the above-identified patent and that said Letters Patent are hereby corrected as shown below:

should be

In Column 22, Line 56 thereof, "4-yl]methylthio]ethyl≡guanidine" should read -- 4-yl)methylthio]ethyl}guanidine --.

Signed and Sealed this

Fourth Day of November 1980

[SEAL]

Attest:

SIDNEY A. DIAMOND

Attesting Officer

Commissioner of Patents and Trademarks